US012023050B2

(12) United States Patent
Flatters et al.

(10) Patent No.: US 12,023,050 B2
(45) Date of Patent: Jul. 2, 2024

(54) ACETABULAR REAMER HANDLE AND METHOD OF REAMING AN ACETABULUM

(71) Applicant: DEPUY IRELAND UNLIMITED COMPANY, Ringaskiddy (IE)

(72) Inventors: Ian Flatters, Sheffield (GB); David Horne, Leeds (GB); Duncan Temple, London (GB)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 214 days.

(21) Appl. No.: 16/969,332

(22) PCT Filed: Jan. 10, 2019

(86) PCT No.: PCT/EP2019/050562
§ 371 (c)(1),
(2) Date: Aug. 12, 2020

(87) PCT Pub. No.: WO2019/161985
PCT Pub. Date: Aug. 29, 2019

(65) Prior Publication Data
US 2021/0015494 A1 Jan. 21, 2021

(30) Foreign Application Priority Data
Feb. 21, 2018 (GB) ...................... 1802789

(51) Int. Cl.
*A61B 17/16* (2006.01)
(52) U.S. Cl.
CPC ...... *A61B 17/1666* (2013.01); *A61B 17/1631* (2013.01)

(58) Field of Classification Search
CPC ............ A61B 17/1631; A61B 17/1633; A61B 17/1666; A61B 17/164; A61B 17/0281; A61B 17/0218
See application file for complete search history.

(56) References Cited

U.S. PATENT DOCUMENTS 7,008,430 B2   3/2006   Dong et al.
7,637,909 B2   12/2009   Lechot
(Continued)

FOREIGN PATENT DOCUMENTS

EP   2954860 A2   12/2015
JP   2005-523764 A   8/2005
(Continued)

OTHER PUBLICATIONS

EP Search Report for PCT/EP2019/050562 dated Apr. 12, 2019.
(Continued)

*Primary Examiner* — Amy R Sipp

(57) ABSTRACT

An acetabular reamer handle including a shaft having a distal end, a neck part having a longitudinal axis, a driveline extending through the shaft and the neck part, and a locking mechanism. A distally located head part of the driveline is mounted for rotation about the longitudinal axis of the neck part and is connectable to a reamer. The distal end of the shaft and a proximal end of the neck part are pivotally attached to allow the shaft to be tilted relative to the longitudinal axis. The tilting can allow part of the acetabulum and/or reamer that is otherwise obscured to be viewed. The locking mechanism includes an engagement member having an engagement surface located at the distal end of the shaft. The engagement member is moveable distally to urge the engagement surface against the proximal end of the neck part.

12 Claims, 7 Drawing Sheets

(56) References Cited

U.S. PATENT DOCUMENTS

| | | |
|---|---|---|
| 7,819,875 B2 | 10/2010 | Chana |
| 8,052,690 B2 | 11/2011 | Berthusen et al. |
| 8,160,345 B2 | 4/2012 | Park |
| 10,105,148 B2 | 10/2018 | Lechot |
| 10,568,649 B2 | 2/2020 | Roger |
| 2004/0097947 A1 | 5/2004 | Wolford |
| 2005/0159751 A1* | 7/2005 | Berthusen .......... A61B 17/1666 606/80 |
| 2010/0023015 A1 | 1/2010 | Park |
| 2015/0313613 A1* | 11/2015 | Rosse ................ A61B 17/1666 606/81 |
| 2015/0320428 A1 | 11/2015 | Roger |

FOREIGN PATENT DOCUMENTS

| | | |
|---|---|---|
| KR | 20160016966 A | 2/2016 |
| WO | 2018033788 A1 | 2/2018 |

OTHER PUBLICATIONS

Japanese Search Report for Corresponding Japanese App. No. 2020-544258, dated Jan. 10, 2023, 6 Pages.

Indian Examination Report for Corresponding Indian Patent Application No. 202017035712, Dated Apr. 7, 2022, 6 Pages.

New Zealand Examination Report for Corresponding New Zealand Patent Application No. 2767376, Dated Jan. 29, 2024, 4 Pages.

Chinese Search Report for Corresponding Chinese Patent Application No. 201980014783, Issued on Dec. 20, 2023, 10 Pages.

\* cited by examiner

ACETABULAR REAMER HANDLE AND METHOD OF REAMING AN ACETABULUM

This application is a National Stage Application filed Under 35 U.S.C. § 371 of International Application No. PCT/EP2019/050562 filed Jan. 10, 2019, which claims priority to GB1802789.6 filed Feb. 21, 2018, both of which are hereby incorporated by reference in their entireties.

FIELD OF THE INVENTION

This invention relates to an acetabular reamer handle. This invention also relates to a method of reaming an acetabulum in a hip replacement procedure.

BACKGROUND OF THE INVENTION

Hip replacement is a surgical procedure in which the hip joint is replaced by a prosthetic implant. As part of a hip replacement procedure, an acetabulum of the patient may be prepared for receiving an acetabular cup implant by reaming it to an appropriate size and depth. A surgical tool for reaming the acetabulum may include a reamer having a substantially hemispherical dome to be received in the acetabulum. The reamer may also include features located on an outer surface of the dome for grating the inner surface of the acetabulum as the reamer rotates. The reamer may be attached to a distal end of a tubular reamer handle, to allow the surgeon to manipulate it (e.g. to position the dome within the acetabulum and to apply a force for pressing the reamer against the inner surface of the acetabulum as the reamer rotates). A driveline may extend within the reamer handle for transmitting torque to the reamer.

Various kinds of reamer handles may be used.

One kind of reamer handle is an offset reamer handle. This kind of reamer handle may include a pair of bends in the tube, forming a dog-leg configuration, which may allow a surgeon to work more easily around soft tissue.

Another kind of reamer handle may include a single bend.

A further kind of reamer handle may be substantially straight (i.e. including no bends).

WO2003/065906 describes a surgical device for holding and rotating an acetabular reaming head. The device comprises a shaft having a length which runs from a first end adapted for holding an acetabular reaming head to a second end. At least part of the shaft is divergent from the axis defined by the first and second ends of the shaft, for example the shaft may include a C-shaped divergent portion. A head held by the device can therefore access the acetabulum in its true anatomical position while avoiding encroachment of the shaft on surrounding body parts.

Visibility is generally rather limited during a hip replacement procedure. For example, when using a reamer handle, it may be difficult for a surgeon to inspect the dome of the reamer while it is located in the acetabulum (e.g. for assessing the reaming depth). While in-situ, the dome may, for instance, be at least partially obscured by soft tissue and/or by the reamer handle. In order to assess the reaming depth, the surgeon may remove the reamer handle and reamer from the incision site, or alternatively may detach the reamer handle from the reamer, so as to view the acetabulum and the reamer with the reamer still in-situ, but in either case this is inconvenient.

U.S. Pat. No. 8,052,690 describes an orthopaedic reamer driver that includes a tubular housing having at least one first positioning feature. A driveshaft within the housing has a drive end. A variable angle cap is pivotally coupled with the housing adjacent the drive end. The variable angle cap includes at least one leg extending along a side of the housing. Each leg has a second positioning feature selectively engaging and disengaging with a corresponding first positioning feature at a selected one of a plurality of angular positions. Each second positioning feature maintains the variable angle cap at the selected angular position when engaged with the corresponding first positioning feature. A variable angle joint is coupled to the drive end, and a reamer drive head is coupled to the variable angle joint.

U.S. Pat. No. 7,008,430 describes a positioning tool for a joint socket cutting instrument or a implant that is designed for use with a minimally invasive surgical procedure and in conjunction with a computer assisted surgical procedure. The positioning tool has a longitudinally extending drive shaft having a moveable joint at a first end and a drive coupling for connecting to a power source at a second end. A holder for mounting a cutting tool such a drill or as an acetabular cutting instrument or for mounting an acetabular implant is coupled to the moveable joint at the first end of the drive shaft for movement with respect to the drive shaft. The holder is rotatable about a central axis thereof when the drive shaft is rotated. The drive shaft includes a shaft bearing mounted thereon which is pivotally coupled to the shaft at a fixed longitudinal position and is pivotally coupled to a longitudinally extending first arm having a handle. A tracker system which is capable of being utilized by a computer-aided surgical system is mounted on the first arm. A second arm is provided which is pivotally connected to the holder at a first end and pivotally connected to the first arm at a second end. The resulting four bar linkage allows the holder and the cutting instrument/implant to be manipulated in any position while the known geometric relationship between the tracker and the holder allows the location of the holder to be displayed by the computer on a cathode ray tube with respect to a joint.

US 2005/159751 A1 describes an orthopaedic reamer driver that includes a tubular housing having at least one first positioning feature. A driveshaft within the housing has a drive end. A variable angle cap is pivotally coupled with the housing adjacent the drive end. The variable angle cap includes at least one leg extending along a side of the housing. Each leg has a second positioning feature selectively engaging and disengaging with a corresponding first positioning feature at a selected one of a plurality of angular positions. Each second positioning feature maintains the variable angle cap at the selected angular position when engaged with the corresponding first positioning feature. A variable angle joint is coupled to the drive end, and a reamer drive head is coupled to the variable angle joint.

WO 2018/033788 A1 describes a surgical reamer driver device that provides a fully closed tube which prevents the invasion of debris and minimizes abrasion of soft tissue during use. The reamer device includes a minimum number of component assemblies, so as to permit easy replacement and minimize wear. The surgical reamer driver has a housing assembly in a stand-alone, assembled unit, a transmission drive train in a stand-alone, assembled unit enclosed in the housing assembly, and having at least one double universal joint and a surgical tool connector at the distal end thereof, a motor shaft coupling in a stand-alone, assembled unit at the proximal end thereof, and a handle assembly in a stand-alone, assembled unit at the proximal end thereof, these four basic components forming a driver which in a fully assembled state effectively prevents debris from access in the inner workings of the driver. A method for disassembling the reamer driver includes the steps of: a. actuating a sliding release sleeve to unlock the handle assembly from the housing assembly, thereby permitting the de-encapsulation of the drive train within the housing assembly; b. sliding the handle assembly off of the housing thereby effectively de-encapsulating the drive train; c. pulling the motor shaft coupling out of the housing thereby freeing the drive train from axial constraint on one end; d. unsnapping the drive train on the one end and lifting the one end out of the housing assembly thereby permitting removal of the drive train; and e. pulling the drive train out of the housing assembly, thus removing the drive train from the housing assembly.

US 2004/097947 A1 describes an orthopaedic reamer assembly for minimally invasive surgery including a reamer and a driver. The driver includes a shaft with a distal end and a longitudinal axis; and a driver head connected to the distal end. The driver head is pivotable about an axis generally perpendicular to the longitudinal axis. The reamer is connected to the driver head.

EP 2 954 860 A2 describes an orthopaedic reamer handle, comprising: a reamer portion configured to transmit torque to a reamer head; a driver portion connected to said reamer portion and configured to receive and transmit torque from a driver; and a drive train connecting said reamer portion and said driver portion and configured to transmit torque from said driver portion to said reamer portion, said drive train including: a first drive shaft having a first end and a second end, said first end being connected to said driver portion, said first drive shaft defining a first axis; a first intermediate connector having a first intermediate end and a second intermediate end, said first intermediate end being connected to said second end; an offsetting member having a third end and a fourth end, said third end being connected to said second intermediate end at an acute angle relative to said first axis, said offsetting member defining a second axis; and a second intermediate connector connecting said fourth end to said reamer portion at an acute angle relative to said second axis.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided an acetabular reamer handle comprising:
a hollow shaft having a distal end;
a hollow neck part having a longitudinal axis;
a driveline extending through the shaft and the neck part, wherein a distally located head part of the driveline is mounted for rotation about the longitudinal axis of the neck part and is connectable to an acetabular reamer, and wherein the distal end of the shaft and a proximal end of the neck part are pivotally attached to allow the shaft to be tilted relative to the longitudinal axis of the neck part; and
a locking mechanism comprising an engagement member having an engagement surface located at the distal end of the shaft, wherein the engagement surface is substantially perimetric to a longitudinal axis of the hollow shaft at the distal end of the shaft, and wherein the engagement member moveable distally to urge the engagement surface against the proximal end of the neck part to resist said tilting of the shaft relative to the longitudinal axis of the neck part.

Tilting of the shaft relative to the longitudinal axis of the neck part can allow a part of the acetabulum and/or reamer otherwise obscured by the reamer handle to be viewed. This may, for instance, allow the surgeon a better view for determining the depth to which the acetabulum has been reamed, without having to remove the reamer and reamer handle from the acetabulum or disconnect the reamer handle from the reamer. The locking mechanism can serve to prevent unwanted tilting of the shaft while the reamer is being operated. The locking mechanism may be simple to operate and may have a compact, robust construction that need not include complicated parts that would otherwise increase the cost of the reamer handle and/or reduce its reliability.

The proximal end of the neck part may include a surface for engagement with the engagement surface of the engagement member. The surface of the proximal end of the neck part may be contained in a plane.

The surface of the proximal end of the neck part may have a surface normal that is oriented at an angle $\alpha$ with respect to the longitudinal axis of the neck part. Typically, a may be less than 90°, to allow correct operation of the driveline. This angling of the neck part relative to the shaft may allow the surgeon to work more easily around soft tissue in the incision site. In some embodiments $30°\leq\alpha\leq60°$. In some embodiments, $\alpha$ is about 30°. In some embodiments, $\alpha$ is about 45°.

The surface of the proximal end of the neck part may contained in a plane having a surface normal that is oriented parallel to the longitudinal axis of the neck part. This can allow the acetabular reamer handle to operate as a straight reamer handle in some embodiments (notwithstanding the ability of the reamer handle to tilt as mentioned above).

The engagement member may be slideably mounted inside the hollow shaft. The engagement member may be configured to protrude from the distal end of the hollow shaft to urge the engagement surface against the proximal end of the neck part. In this way, the components of the locking mechanism may be protected by the wall of the shaft, in which case fluids and/or bone fragments in the incision site would not interfere with their operation.

The engagement member may be resiliently biased distally to urge the engagement surface against the proximal end of the neck part. To implement this, the locking mechanism may include a helical spring mounted coaxially with respect to the distal end of the hollow shaft and proximally with respect to the engagement member. The helical spring may be mounted inside the hollow shaft. Again, this may protect the spring from interference by fluids and/or bone fragments in the incision site.

The engagement member may include a handle part for manually retracting the engagement member in a proximal direction to release the engagement surface from the proximal end of the neck part. This can allow the surgeon selectively to release the shaft to allow it to be tilted, while keeping the shaft is locked down during operation of the reamer.

The acetabular reamer may include one or more locking members extending from the engagement surface to be received within one or more corresponding openings in the proximal end of the neck part. This arrangement can allow the locking of the engagement surface against the proximal end of the neck part to resist the tilting of the shaft relative to the longitudinal axis of the neck part. Where more than one such locking member is provided, they may be distributed (e.g. evenly) around the perimeter formed by the engagement surface of the engagement member. For instance, the acetabular reamer may include two locking member, one being located on either side of the plane containing the hollow shaft and the longitudinal axis of the hollow neck part.

The driveline may include a universal joint located at the pivot point between the distal end of the shaft and the proximal end of the neck part. This can allow an angle between the neck part (within which the head part my rotate) and the shaft to be accommodated.

The acetabular reamer handle may be an offset acetabular reamer handle in which the hollow shaft includes a proximal shaft section and a distal shaft section, and in which the shaft has a bend located at an interface between the proximal shaft section and the distal shaft section. The proximal shaft section and the distal shaft section may be rigidly formed whereby the angle between the longitudinal axis of the distal shaft section and a longitudinal axis of the proximal shaft section may be fixed.

The engagement surface may be substantially ring shaped, triangular, rectangular, pentagonal or hexagonal.

According to another aspect of the invention, there is provided a surgical kit comprising the acetabular reamer handle of the kind set out above and one or more differently sized acetabular reamers connectable to the head part of the acetabular reamer handle.

According to a further aspect of the invention, there is provided a method of reaming an acetabulum of a patient using a reamer connected to a reamer handle, the reamer handle comprising:
  a hollow shaft having a distal end;
  a hollow neck part having a longitudinal axis;
  a driveline extending through the shaft and the neck part, wherein a distally located head part of the driveline is mounted for rotation about the longitudinal axis of the neck part and is connected to the reamer, and wherein the distal end of the shaft and a proximal end of the neck part are pivotally attached to allow the shaft to be tilted relative to the longitudinal axis of the neck part;
the method comprising:
  inserting the reamer into the acetabulum;
  operating the reamer to remove bone from a surface of the acetabulum; and
  with the reamer located in the acetabulum, tilting the shaft relative to the longitudinal axis of the neck part to view a part of the acetabulum and/or reamer otherwise obscured by the reamer handle.

Tilting of the shaft relative to the longitudinal axis of the neck part can allow a part of the acetabulum and/or reamer otherwise obscured by the reamer handle to be viewed without having to remove the reamer and reamer handle from the acetabulum or having to disconnect the reamer handle from the reamer.

The method may further include tilting the reamer handle about the longitudinal axis of the neck part to view a part of the acetabulum and/or reamer otherwise obscured by the reamer handle.

The method may further include viewing the part of the acetabulum and/or reamer otherwise obscured by the reamer handle to determine a depth of the reaming.

The method may further include operating a locking mechanism of the reamer handle to disengage an engagement member of the locking mechanism from the proximal end of the head part to allow tilting of the shaft relative to the longitudinal axis of the neck part.

The engagement member may be moveable distally to urge the engagement surface against the proximal end of the neck part to resist the tilting of the shaft relative to the longitudinal axis of the neck part.

The engagement member may be resiliently biased toward the proximal end of the head part. This may be implemented with a helical spring, as noted above.

The engagement member may be slideably mounted on or in the shaft. The method may further include manually retracting the engagement member in a proximal direction to release the engagement member from the proximal end of the neck part.

The engagement member may have an engagement surface located at the distal end of the shaft for engaging with the proximal end of the neck part to resist the tilting of the shaft relative to the longitudinal axis of the neck part. The engagement surface may be substantially perimetric to a longitudinal axis of the hollow shaft at the distal end of the shaft.

The engagement surface may be substantially ring shaped, triangular, rectangular, pentagonal or hexagonal.

The reamer handle may be an offset reamer handle in which the hollow shaft includes a proximal shaft section and a distal shaft section, and in which the shaft has a bend located at an interface between the proximal shaft section and the distal shaft section.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Figure 1A:
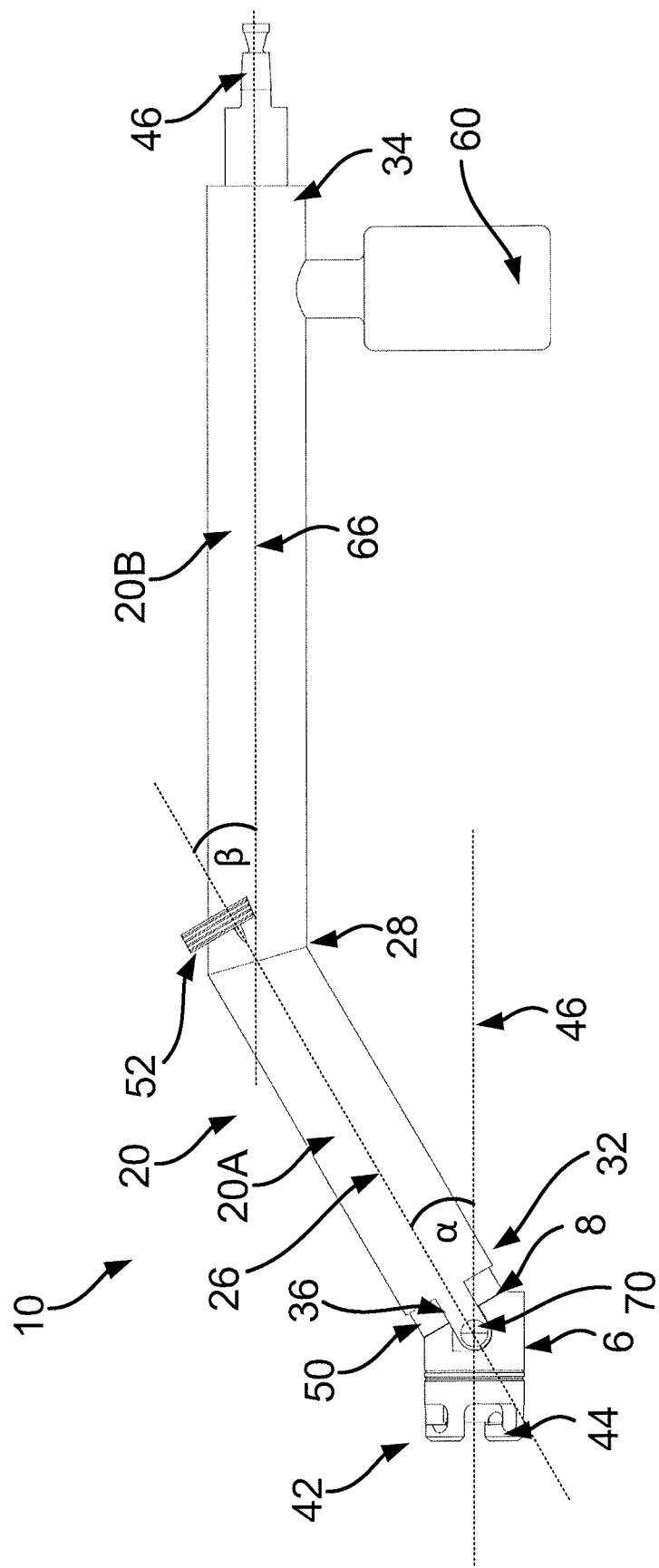
FIG. 1A shows a side view of an acetabular reamer handle according to an embodiment of this invention.

Embodiments of the present invention are described in the following with reference to the accompanying drawings.

FIGS. 1 to 7 show various views of an acetabular reamer handle 10 according to an embodiment of this invention.

The acetabular reamer handle 10 includes a shaft 20. The shaft 20 has a proximal end 34 and a distal end 32. The shaft 20 is substantially hollow (see, for example, the cross section of FIG. 2).

In this embodiment, the shaft 20 includes a distal shaft section 20A and a proximal shaft section 20B. The shaft sections 20A, 20B are fixedly joined together at a bend 28 in the shaft 20, whereby a longitudinal axis 26 of the distal shaft section 20A is oriented at an angle β (see e.g. FIG. 1A) to a longitudinal axis 66 of the proximal shaft section 20B. Each shaft section 20A, 20B may have a distal end and a proximal end. In the present embodiment, the proximal end of the distal shaft section 20A is joined at the aforementioned bend 28 to the distal end of the proximal shaft section 20B. The angle β may be in the range 30°≤β≤60°. In particular, it is envisaged that in some embodiments, β=30° or α=45°.

It is also envisaged that the shaft 20 may be substantially straight, without a bend of the kind shown in the figures of the present embodiment.

The shaft 20 (including e.g. its constituent shaft sections 20A, 20B) may be generally elongate, cylindrical in shape and may have a substantially circular cross section.

One or more handle parts 60 may be provided on the shaft 20 to facilitate holding the acetabular reamer handle 10 and to allow an axial force to be applied by a surgeon, for urging a reamer attached to the distal end of the acetabular reamer handle 10 into the inner surface of the acetabulum of a patient during reaming. As shown in the figures, each handle part 60 may extend radially outward from the side of one of the shaft 20. A handle part 60 may be located toward the proximal end of the shaft 20. In the present embodiment, the acetabular reamer handle 10 includes a single handle part 60, which extends radially outward from the side of the additional shaft section 20B.

The acetabular reamer handle 10 also includes a neck part 6. The neck part 6 is substantially hollow. The neck part 6 may be substantially cylindrical and may have a substantially circular cross section. The neck part 6 has a proximal end 62, a distal end 64 and a longitudinal axis 46. As will be described in more detail below, the proximal end 62 of the neck part 6 is pivotally connected to the distal end 32 of the shaft 20, to allow the shaft 20 to be tilted relative to the longitudinal axis 46 of the neck part 6.

The acetabular reamer handle 10 also includes a driveline 40. The drive line 40 is shown in full in the exploded view of FIG. 7 and parts of the drive line 40 are also visible in FIGS. 1A, 1B, 3, 5, 8 and 9. For the purposes of clarity, only a head part 42 (to be described below) of the driveline 40 is shown in the cross sections of FIGS. 2, 4 and 6. The driveline 40 is elongate and dimensioned to fit inside and extend through the hollow shaft 20 and neck part 6.

The driveline 40 may include a plurality of driveline sections. In general, in embodiments where the shaft 20 includes one or more bends such as bend 28, the driveline 40 may include a respective driveline section for each shaft section of the hollow shaft 20. In the present embodiment, these driveline sections include a distal driveline section 40A and a proximal driveline section 40B. To accommodate any bends in the shaft 20 (and also the angle between the shaft 20 and the neck part 6, to be described below) the driveline 40 may include one or more universal joints positioned along its length. In the present embodiment, the driveline 40 includes a first universal joint 48A joining a proximal end of the head part 42 of the drive line 40 to a distal end of the distal driveline section 40A and a second universal joint 48B connecting a proximal end of the distal driveline section 40A to a distal end of the additional driveline section 40B.

Figure 1B:
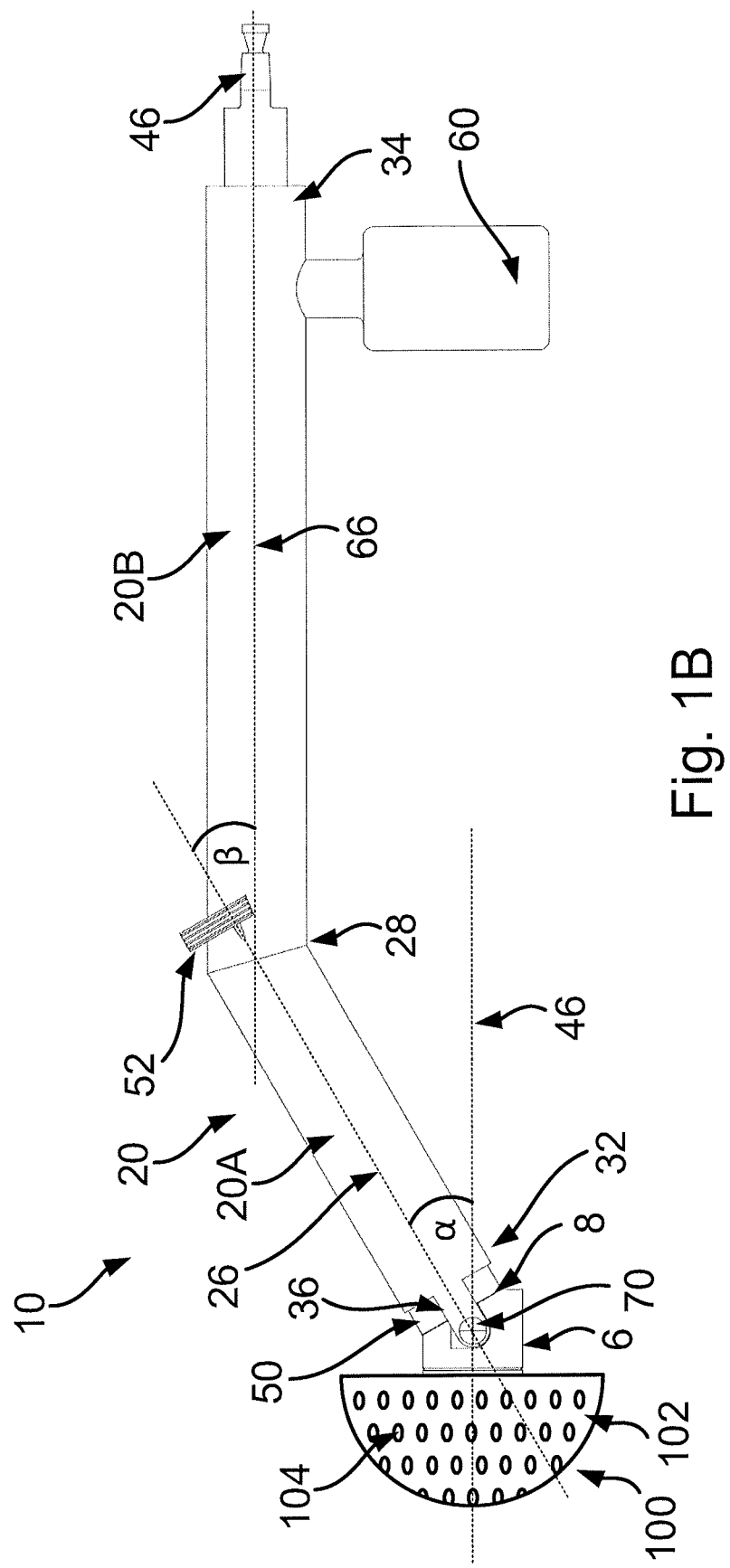
FIG. 1B shows a side view of the acetabular reamer handle of FIG. 1, with an acetabular reamer connected to a distally located head part of a driveline of the acetabular reamer handle.
Figure 2:
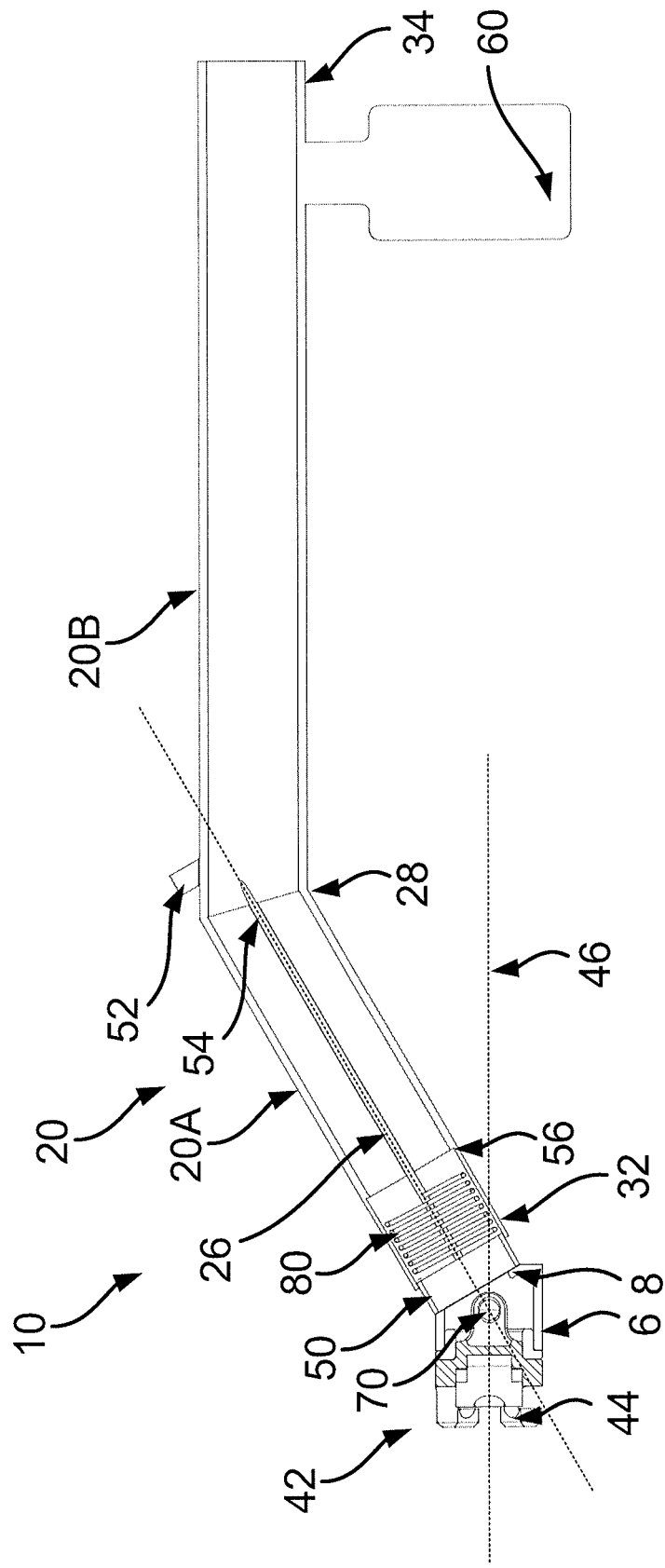
FIG. 2 shows a cross section of the acetabular reamer handle of FIG. 1A.
Figure 3:
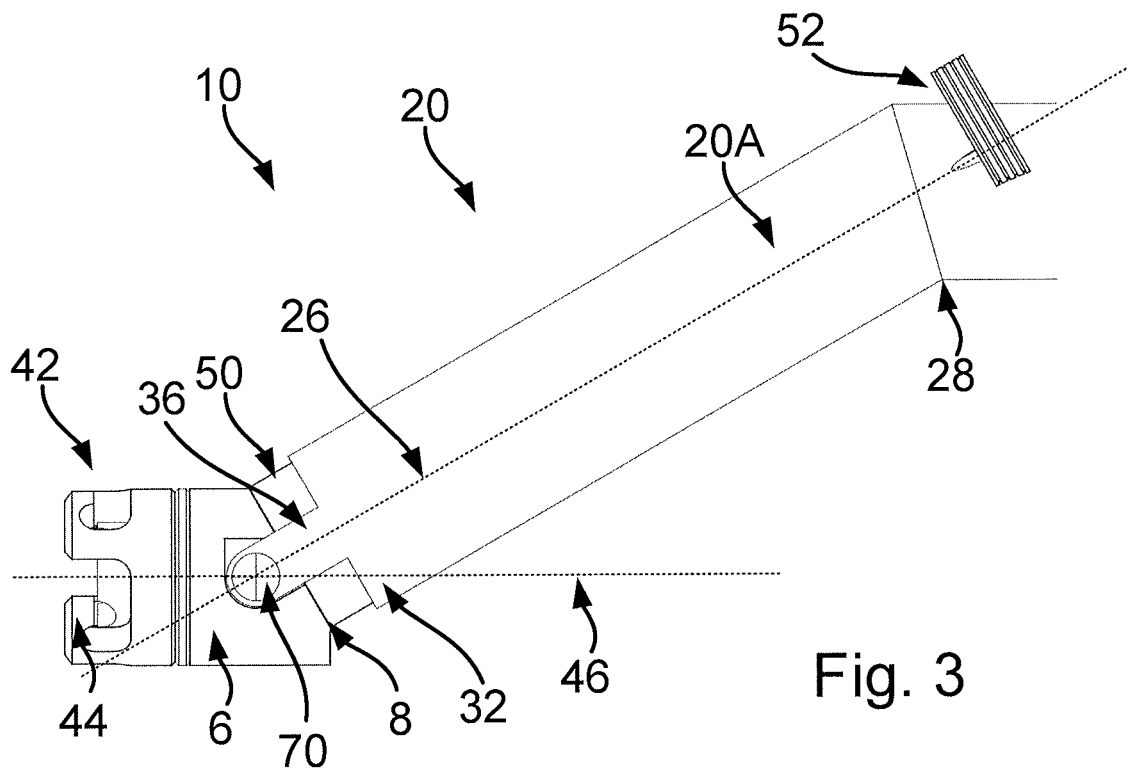
FIG. 3 shows a close up view of the components located toward to the distal end of the shaft of the acetabular reamer handle of FIG. 1A.
Figure 4:
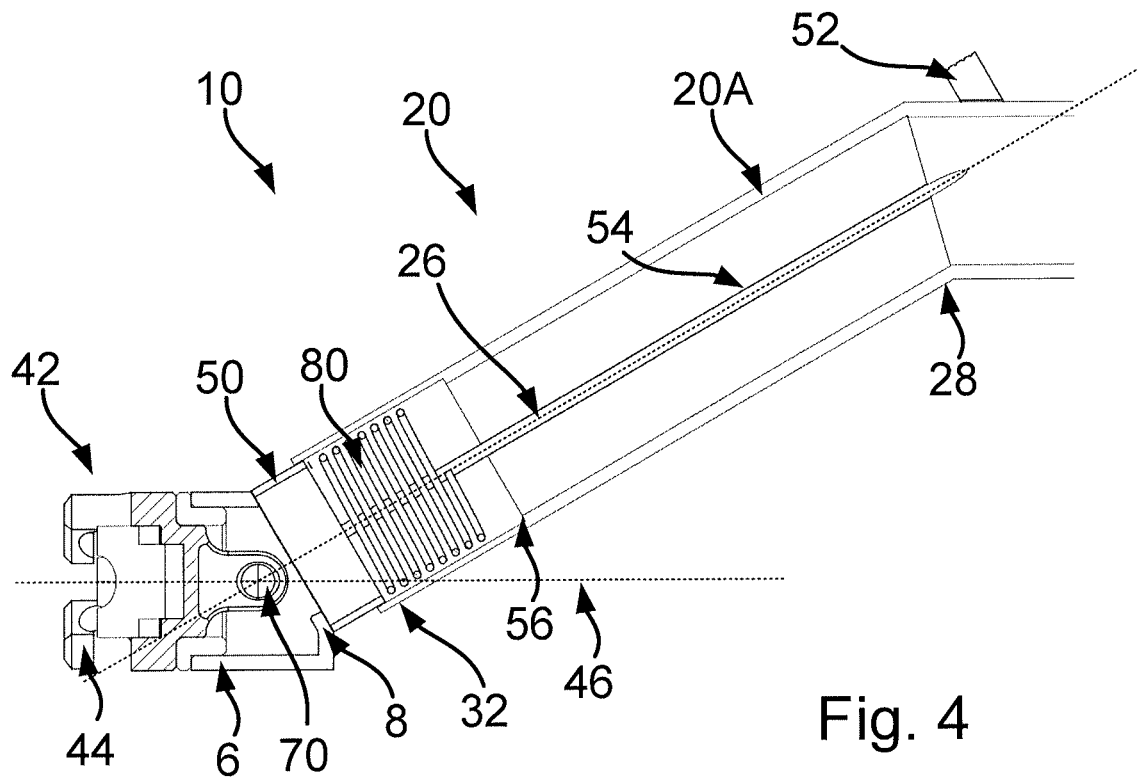
FIG. 4 shows a close up cross section of the components located toward to the distal end of the shaft of the acetabular reamer handle of FIG. 1A.

The proximal end 34 of the shaft 20 of the acetabular reamer handle 10 (which is formed by the additional shaft section 20B in the present embodiment having two shaft sections) may have an opening through which a proximal end 45 of the driveline 40 may protrude. The proximal end 45 of the driveline 40 may include connection features for connection to a power tool such as a rotational driver for applying torque to the driveline 40. In use, the driveline 40 rotates to transmit the torque through the hollow shaft 20 and neck part 6 to the distally located head part 42 of the drive line 40. The head part 42 of the drive line 40 is connectable to a reamer 100. FIG. 1B shows a side view of the acetabular reamer handle 10 of FIG. 1, with an acetabular reamer 100 connected to the head part 42 of the driveline 40. To implement the connection between the head part 42 and the acetabular reamer 100, the head part 42 may include distally located connection features 44 for connection with corresponding connection features of the acetabular reamer 100. As shown in FIG. 1B, the acetabular reamer 100 may, for instance comprise a hemispherical dome 102 for insertion into the acetabulum of a patient. An outer surface of the dome 102 may include features 104 for grating bone away from the inner surface of the acetabulum as the acetabular reamer 100 rotates with the driveline 40.

The head part 42 is mounted for rotation about a longitudinal axis 46 of the neck part 6. The axis of rotation of the head part 42 may generally be coaxial with the longitudinal axis 46. In the present example, a proximal end of the head part 42 is located inside the neck part 6. An outer surface of the head part 42 (e.g. of the proximal end of the head art in the present embodiment) may form a snug fit with an inner surface of the neck part 6, so that the head part 42 rides within the neck part 6, to maintain the coaxial relationship between the axis of rotation of the head part 42 and the longitudinal axis 46. In the present embodiment, the distal end of the head part 42 protrudes distally from the distal end 64 of the neck part 6 and includes the aforementioned connection features 44 for connection to an acetabular reamer. The distal end of the head part 42 may be generally cylindrical and may have a larger diameter than the proximal end of the head part 42, which rotates within the neck part 6. In this embodiment, the distal end of the head part 42 has the same outer diameter as the distal end 62 of the neck part 6, so that the distal end of the head part 42 is flush with the outer surface of the distal end 62 of the neck part 6.

In embodiments where the shaft 20 includes one or more bends, the shaft sections may be of different lengths (as measured along their longitudinal axes). For instance, in the present embodiment, the distal shaft section 20A is shorter than the additional shaft section 20B. The head part 42 may be shorter (as measured along its longitudinal axis 46) than the shaft sections.

Figure 7:
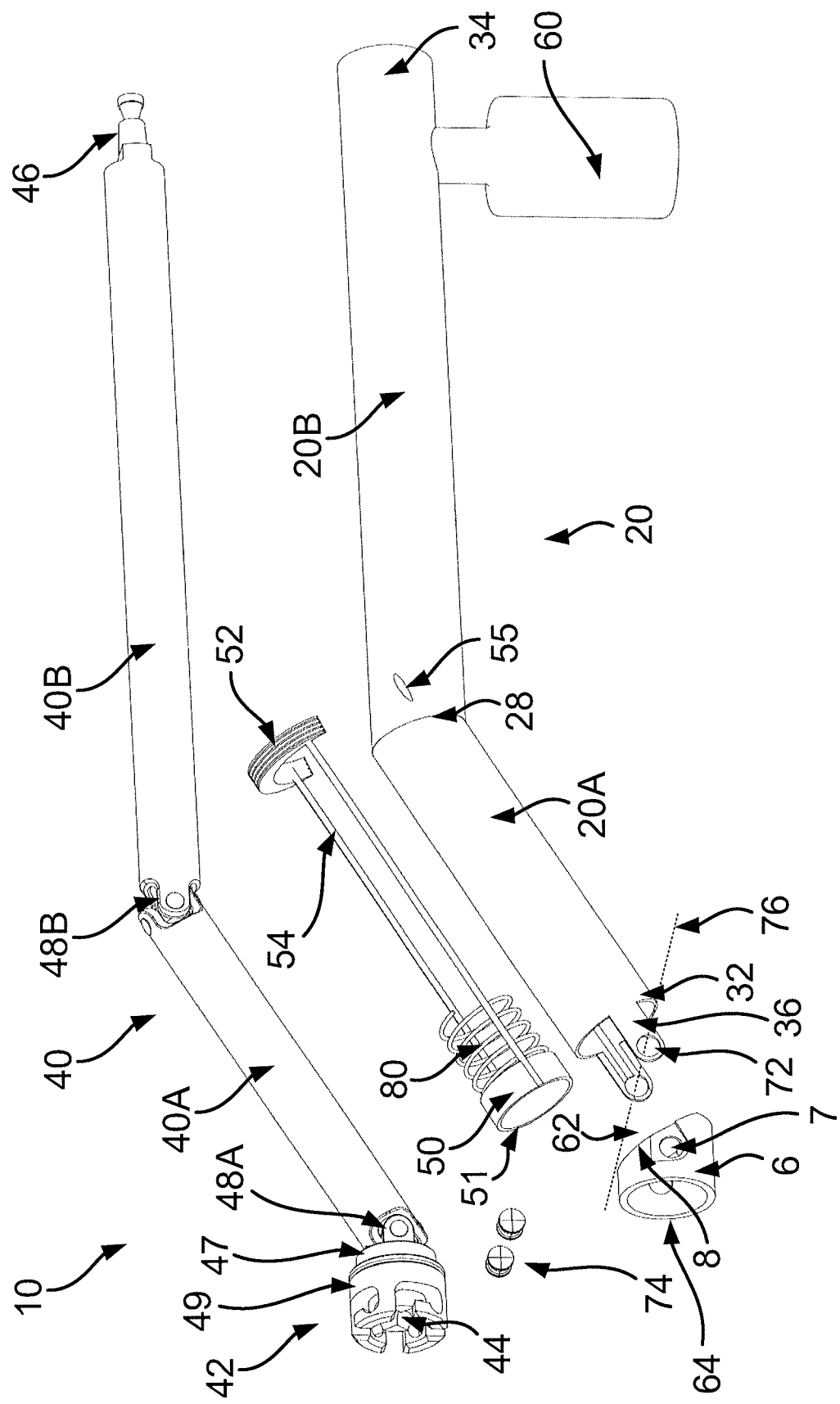
FIG. 7 shows an exploded view of the acetabular reamer handle of FIG. 1A.

As mentioned previously, the proximal end 62 of the neck part 6 is pivotally connected to the distal end 32 of the shaft 20. In the present embodiment, the pivotal connection 70 is formed by a pair of holes 72 located at the distal end 32 of the shaft 20 and a pair of corresponding holes 7 located on the neck part 6, through which bolts 74 pass. The axis of rotation 76 provided by the pivotal connection 70 is generally perpendicular to both the longitudinal axis 46 of the neck part 6 and the longitudinal axis 26 of the distal end 32 of (e.g. the distal shaft section 20A) the shaft 20. As shown in FIG. 7, the holes 72 may be located at the ends of a pair arms 36 that extend distally from the end of the shaft 20.

These arms 36 can provide clearance between the hollow cylindrical part of the shaft 20 and the proximal end 62 of the neck part 6, to allow relative rotation of the shaft 20 and the neck part 6 about the pivotal connection 70.

Figure 5:
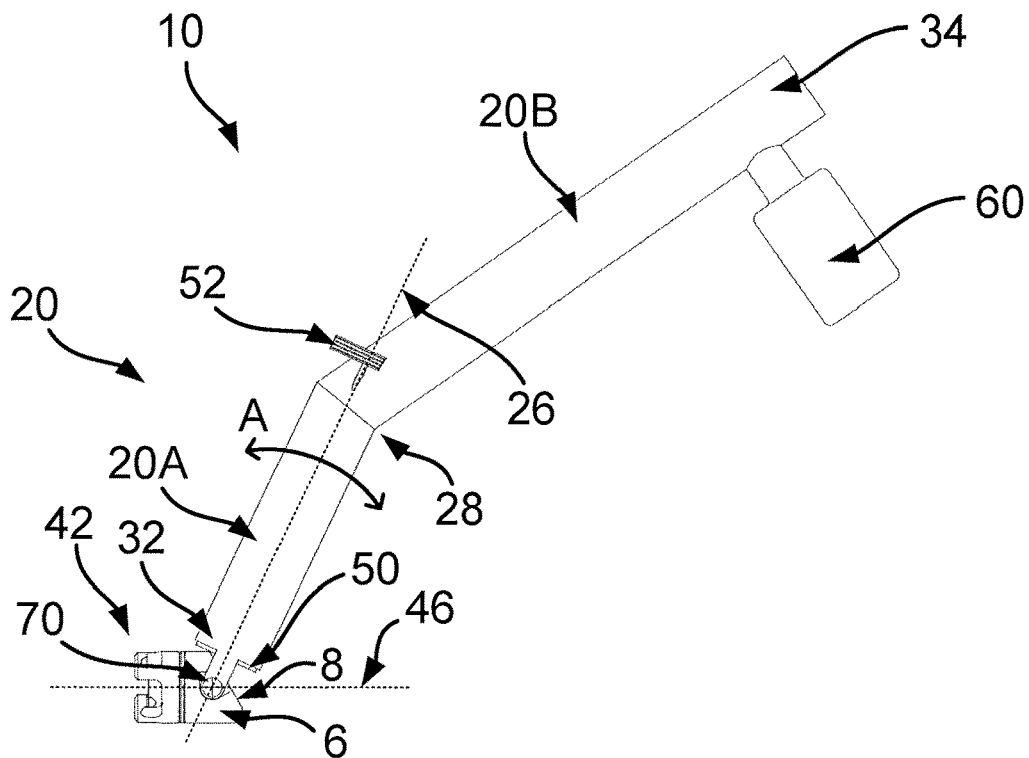
FIG. 5 shows another side view of the acetabular reamer handle of FIG. 1A.
Figure 6:
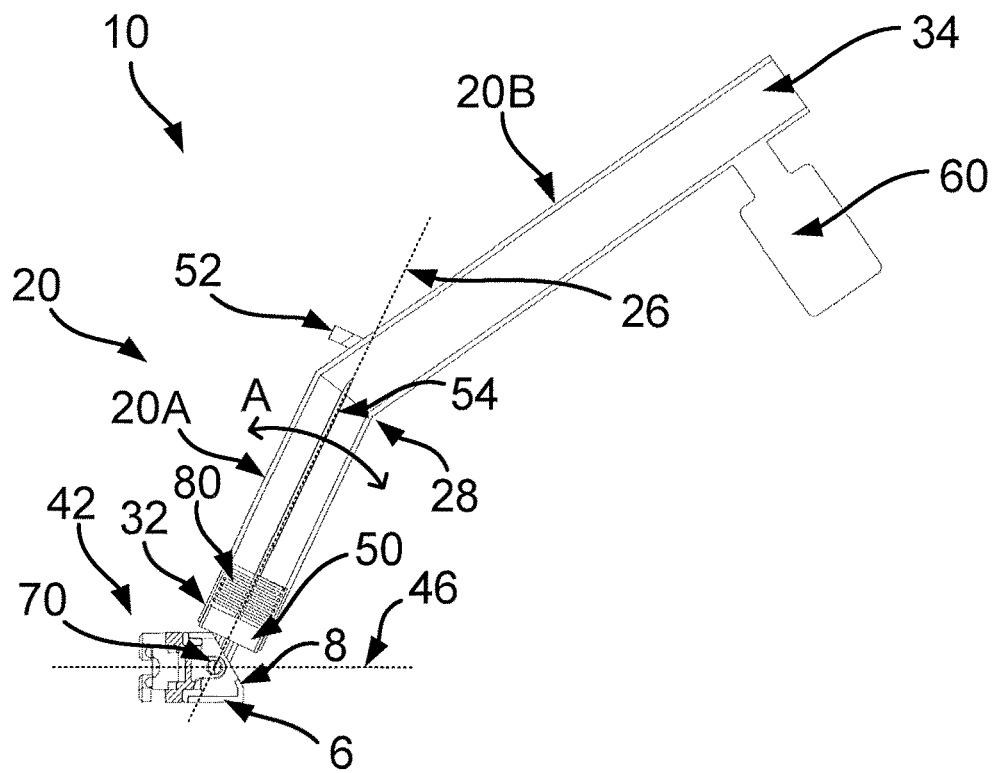
FIG. 6 shows another cross section of the acetabular reamer handle of FIG. 1A.

The pivotal connection 70 between the neck part 6 and the shaft 20 can allow the shaft 20 to be tilted relative to the longitudinal axis 46 of the neck part 6. This tilting of the shaft 20 relative to the longitudinal axis 46 of the neck part 6 can allow a part of the acetabulum and/or reamer 100 otherwise obscured by the reamer handle 10 to be viewed. This may, for instance, allow the surgeon a better view for determining the depth to which the acetabulum has been reamed, without having to remove the reamer 100 and reamer handle 10 from the acetabulum or having to disconnect the reamer handle 10 from the reamer. FIGS. 1 to 4 show the acetabular reamer handle 10 of the present embodiment in a non-tilted state. FIGS. 5 and 6 show the shaft 20 tilted (in an anti-clockwise direction as viewed in those Figures) so that the angle between the longitudinal axis 46 of the neck part 6 and the longitudinal axis 26 of the distal shaft section 20A is increased in size. From comparison of FIGS. 1 to 4 with FIGS. 5 and 6, it will be appreciated that the tilting of the shaft 20 in this way may allow parts of the acetabulum and/or reamer 100 laying beneath the shaft 20 to be revealed.

Note that the universal joint 48A of the driveline 40 is positioned to coincide with the pivotal connection 70 between the distal end 32 of the shaft 20 and the proximal end 62 of the neck part 6. This can allow the angling of the shaft 20 relative to the longitudinal axis 46 of the neck part 6 to be accommodated. As described herein, this angling of the shaft 20 relative to the longitudinal axis of the neck part 6 may be present in an untilted state of the acetabular reamer handle 10 (e.g. due to the angling of the engagement surface 8 to be described below). The universal joint 48A can also accommodate relative rotation of the shaft 20 and the neck part 6 about the pivotal connection 70 for tilting the shaft as described above.

In addition to the tilting of the shaft 20 as shown in FIGS. 5 and 6, it is envisaged that the shaft 20 may be tilted about the longitudinal axis 46 of the neck part 6 (i.e. either in a clockwise or in an anti-clockwise direction when viewed along the longitudinal axis 46 from the point of view of the surgeon), again to view a part of the acetabulum and/or reamer otherwise obscured by the reamer handle 10.

The pivotal connection 70 between the neck part 6 and the distal end 32 of the shaft 20 may include a locking mechanism. The locking mechanism can serve to resist unwanted tilting of the shaft 20 relative to the longitudinal axis 46 of the neck part 6. In this way, the relative orientations of the neck part 6 and shaft 20 may be fixed in place while the acetabulum of the patient is being reamed. As will be described below, the locking mechanism may be simple to operate and may have a compact, robust construction that need not include complicated parts that would otherwise increase the cost of the reamer handle 10 and/or reduce its reliability.

In this embodiment, the locking mechanism includes an engagement member 50 having an engagement surface 51. As may be appreciated from a comparison of, for example, FIGS. 1 and 7, the engagement surface 51 is substantially perimetric to a longitudinal axis of the hollow shaft at the distal end of the shaft (in the present embodiment, this axis corresponds to the longitudinal axis 26 of the distal shaft section 20A). The engagement member 50 is located at the distal end 32 of the shaft 20. The engagement surface 51 in this embodiment is substantially ring shaped. It is also envisaged that the engagement surface may have a different shape (for example, triangular, rectangular, pentagonal or hexagonal). The engagement member 50 may be substantially tubular and may have a cross sectional shape that corresponds to the shape of the engagement surface 51.

The driveline 40 may pass through a centre of the engagement member 50. The engagement member 50 may be mounted inside or outside the shaft 20. In one embodiment, the engagement member 50 may be mounted as a sleeve on an outer surface of the distal shaft section 20A.

In the present embodiment, the engagement member 50 is slideably mounted inside the shaft 20 and protrudes from the distal end 32 of the shaft 20 to engage with the proximal end 62 of the neck part 6.

The engagement member 50 is moveable distally to urge the engagement surface 51 against the proximal end of the neck part 6 to resist tilting of the shaft 20 relative to the longitudinal axis 46 of the neck part 6.

In one embodiment, the engagement member 50 may be mounted on a screw thread (including a first thread located on the shaft and a second thread located on the engagement member 50), to allow the engagement member to be moved distally (by rotation of the engagement member 50 about the screw thread in a first direction) to urge the engagement surface 51 against the proximal end of the neck part 6. By rotating the engagement member 50 in a second direction, opposite the first direction, the engagement member 50 may be moved proximally, to disengage the engagement surface 51 from the proximal end of the neck part 6.

In other embodiments, the engagement member 50 may be resiliently biased distally to urge the engagement surface 51 against the proximal end of the neck part 6. For instance, in the present embodiment, the locking mechanism includes a spring, such as a helical spring 80. The helical spring 80 may be mounted coaxially with respect to the distal end 32 of the shaft 20 and proximally with respect to the engagement member 50. In embodiments in which the engagement member 50 is mounted as a sleeve outside the shaft 20, the helical spring 80 may also be mounted on the outside of the shaft 20. In the present embodiment, the helical spring 80 is located inside the shaft 20 along with the engagement member 50. As shown in the Figures, the helical spring 80 in this embodiment is located between the engagement member 50 and a circumferential lip 56 provided on an inner surface of the shaft 20 (e.g. FIG. 4). The helical spring 80 is thus arranged to bias the engagement member 50 distally, so that it protrudes from the distal end 32 of the shaft 20 as mentioned above.

In use, the engagement surface 51 of the engagement member 50 is urged against the proximal end 62 of the neck part 6 (e.g. by the spring of the locking mechanism). This resists any pivotal movement of the neck part 6 relative to the shaft 20 (including the tilting of the shaft 20 discussed above).

In this embodiment, the proximal end 62 of the neck part 6 is provided with an engagement surface 8 against which the engagement surface 51 of the engagement member 50 may urge to resist the above mentioned tilting of the shaft 20. The engagement surface 8 and also the engagement surface 51 may be substantially flat, so as to provide stable and secure contact between them.

As can seen from the figures, in this embodiment, the engagement surface 8 of the neck part 6 may be set at an angle to the longitudinal axis 46. In particular, the engagement surface 8 may be contained in a plane having a surface normal that is oriented at a non-zero angle α with respect to the longitudinal axis 46 of the neck part 6. Typically, α may be less than 90°, to allow correct operation of the universal joint 48A, of the driveline 40. This angling of the neck part 6 relative to shaft 20 may allow the surgeon to work more easily around soft tissue in the incision site. In its non-tilted position (e.g. FIG. 1A), the longitudinal axis 26 of the distal end 32 of the shaft 20 may be parallel with the surface normal of the engagement surface 8.

In some embodiments 30°≤α≤60°. In some embodiments, α is about 30°. In some embodiments, α is about 45°.

It is noted that in embodiments in which the shaft 20 includes a bend such as the bend 28, the (untilted) angling of the neck part 6 with respect to the shaft 20 and the bend 28 may combine to configure the acetabular reamer handle 10 as an offset reamer handle. It is envisaged that angle α and β may be equal in size and opposite in direction, to form a dog-leg arrangement in which the longitudinal axis 46 of the neck part 6 is substantially parallel to the longitudinal axis 66 of the proximal shaft section 20B.

In accordance with an alternative embodiment, it is envisaged that the engagement surface 8 of the neck part 6 may be contained in a plane having a surface normal that is oriented parallel to the longitudinal axis 46 of the neck part 6. This can allow the acetabular reamer handle 10 to operate as a straight reamer handle (notwithstanding the ability of the reamer handle to tilt as discussed herein).

To release the engagement surface 51 from the proximal end 62 of the neck part 6, the engagement member 50 may be retracted in an proximal, axial direction, against the bias provided by the spring 80. The engagement member 50 may include, or be connected to, a handle 52, which may include one or more gripping surfaces. The handle 52 can be gripped by the surgeon and retracted in the proximal direction in order to retract the engagement member 50. In the present embodiment, the handle 52 is connected to the engagement member 50 by a pair of arms 54 that extend substantially parallel to the distal end 32 of the shaft 20. The arms 54 extend through respective holes 55 located in the wall of the shaft 20, whereby the handle 52 may be located outside the shaft 20 for operation by the surgeon.

When the proximal end 62 (e.g. the engagement surface 8) is released from the engagement surface 51 by retraction of the engagement member 50, the neck part 6 and the shaft 20 are able freely to pivot about the pivotal connection 70, whereby the shaft 20 may be freely tilted as described herein to view parts of the acetabulum and/or reamer 100 that may otherwise be obscured. After having viewed the acetabulum and/or reamer, the surgeon may return the shaft 20 to its original position (e.g. with the longitudinal axis 26 of the distal end 32 of the shaft 20 laying parallel with the surface normal of the engagement surface 8) and release the handle 52, so that the engagement surface 51 re-engages with, and urges against the proximal end 62 of the neck part 6. In this way, the surgeon may resume reaming, with the shaft 20 is locked down to prevent unwanted tilting.

Figure 8:
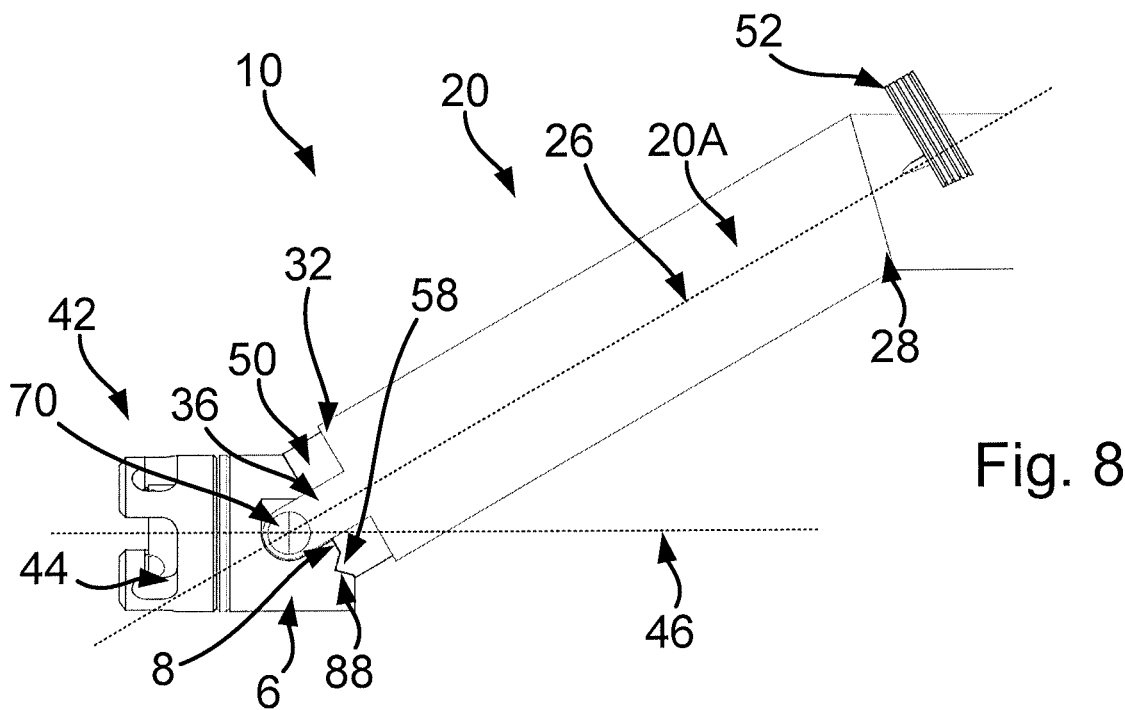
FIG. 8 shows a close up view of the components located toward to the distal end of the shaft of an acetabular reamer handle according to another embodiment of the invention.
Figure 9:
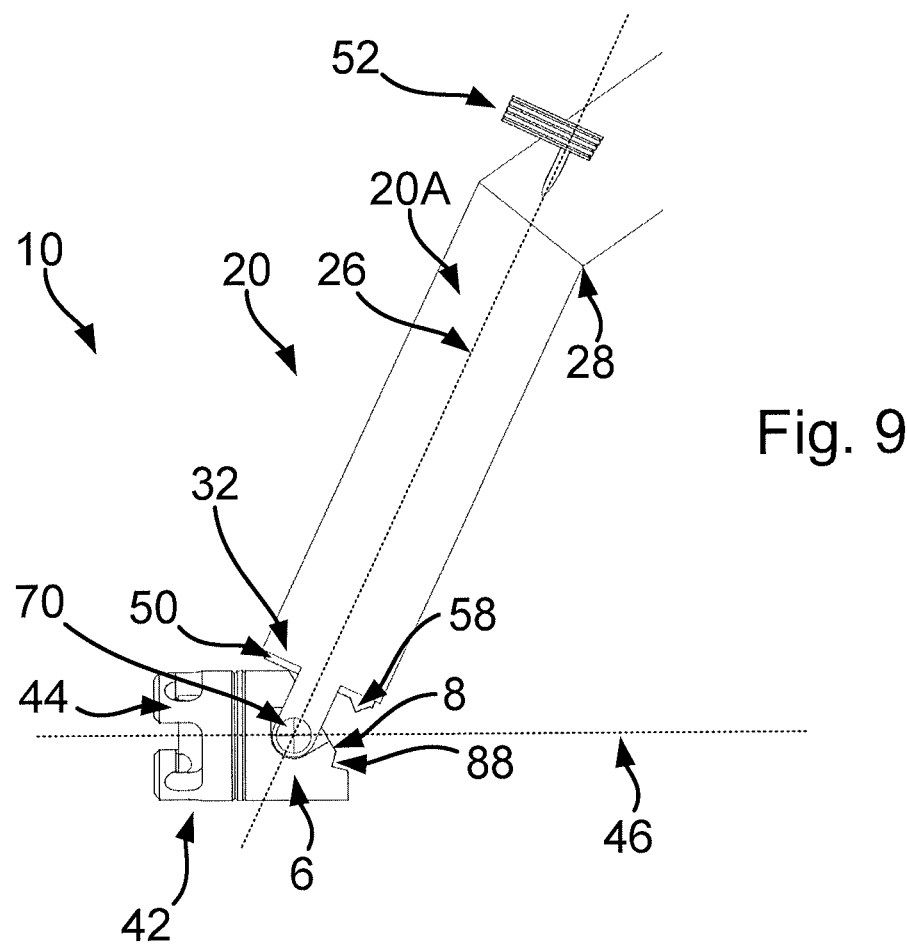
FIG. 9 shows another close up view of the components located toward to the distal end of the shaft of the acetabular reamer handle of FIG. 8.

FIGS. 8 and 9 show the components located toward to the distal end 32 of the shaft 20 of an acetabular reamer handle 10 according to another embodiment of the invention. The embodiment of FIGS. 8 and 9 is similar in many respects to the embodiment of FIGS. 1 to 7, and only the differences will be described below in detail. Note that, like FIGS. 3 and 4, and 5 and 6, FIGS. 8 and 9 show the acetabular reamer handle 10 in an untilted configuration (FIG. 8) for reaming, and in a tilted configuration (FIG. 9) for viewing parts of the acetabulum and/or reamer 100 that would otherwise be obscured by the acetabular reamer handle 10.

In this embodiment, the acetabular reamer handle 10 includes one or more locking members 58. The locking member(s) 58 extends distally from the substantially ring shaped engagement surface 51 of the engagement member 50. As shown in FIG. 8, the locking member(s) 58 can be received within corresponding respective opening(s) 88 located in the proximal end 62 of the neck part 6 (e.g. in the engagement surface 8). The locking member(s) 58 and opening(s) 88 may cooperate to lock down the engagement surface 51 against the proximal end 62 of the neck part 6. In particular, because of the distally protruding orientation of the locking member(s) 58, when the locking member(s) 58 are located in their corresponding opening(s) 88, any attempt to tilt the shaft 20 with respect to the longitudinal axis 46 of the neck part 6 causes the locking member(s) 58 to urge laterally against a sidewall of their corresponding opening(s) 88. The locking member(s) 58 can therefore resist tilting of the shaft 20 when they are received within their corresponding opening(s) 88. Conversely, when the engagement member 50 is retracted proximally as described above, the locking member(s) 58 are withdrawn from their corresponding opening(s) 88, whereby the shaft 20 may be tilted as demonstrated in FIG. 9.

The locking member(s) 58 may be triangular in cross section, with the apex of the triangle pointing distally. In the present embodiment, the apex of the substantially triangular locking member(s) 58 points distally along the longitudinal axis 26 of the distal shaft section 20A. The opening(s) 88 may have an inner surface that conforms to the shape of their corresponding locking member(s) 58.

Where more than one such locking member 58 is provided, these locking members 58 may be distributed (e.g. evenly) around the perimeter formed by the engagement surface 51 of the engagement member 50. For instance, the acetabular reamer 10 may include two locking members 58, one being located on either side of the plane containing the hollow shaft 20 and the longitudinal axis 46 of the hollow neck part 6.

An acetabular reamer handle 10 according to an embodiment of this invention may be included in a surgical kit. The kit may also include one or more differently sized acetabular reamers 100 connectable to the head part of the driveline of the acetabular reamer handle.

In one embodiment, a method of reaming an acetabulum of a patient may include connecting an acetabular reamer 100 to a reamer handle 10 of the kind described above. The method may also include inserting the acetabular reamer 100 into the acetabulum of a patient. The method may also include operating the acetabular reamer 100 to remove bone from a surface of the acetabulum. The method may further include, with the acetabular reamer 100 located in the acetabulum, tilting the shaft 20 relative to the longitudinal axis 46 of the neck part 6 to view a part of the acetabulum and/or acetabular reamer 100 otherwise obscured by the reamer handle 10. The method may also include tilting the reamer handle 10 about the longitudinal axis 46 of the neck part to view a part of the acetabulum and/or acetabular reamer 100 otherwise obscured by the reamer handle 10. By viewing the part of the acetabulum and/or acetabular reamer 100 otherwise obscured by the reamer handle 10, a depth of the reaming may be determined.

The method may also include operating a locking mechanism of the reamer handle 10 to disengage the engagement member 50 of the locking mechanism from the proximal end of the head part 42 to allow the above mentioned tilting of the shaft 20 relative to the longitudinal axis 46 of the neck part.

The method may further include manually retracting the engagement member 50 in a proximal direction to release the engagement member 50 from the proximal end 62 of the neck part 6, as described in more detail above.

Accordingly, there has been described an acetabular reamer handle including a shaft having a distal end, a neck part having a longitudinal axis, a driveline extending through the shaft and the neck part, and a locking mechanism. A distally located head part of the driveline is mounted for rotation about the longitudinal axis of the neck part and is connectable to a reamer. The distal end of the shaft and a proximal end of the neck part are pivotally attached to allow the shaft to be tilted relative to the longitudinal axis. The tilting can allow part of the acetabulum and/or reamer that is otherwise obscured to be viewed. The locking mechanism includes an engagement member having an engagement surface located at the distal end of the shaft. The engagement member is moveable distally to urge the engagement surface against the proximal end of the neck part.

Although particular embodiments of the invention have been described, it will be appreciated that many modifications/additions and/or substitutions may be made within the scope of the claimed invention.

The invention claimed is:

1. An acetabular reamer handle comprising:
   a hollow shaft having a distal end and a wall with pair of holes extending therethrough;
   a hollow neck part having a longitudinal axis;
   a driveline extending through the shaft and the neck part, wherein a distally located head part of the driveline is mounted for rotation about the longitudinal axis of the neck part and is connectable to an acetabular reamer, and wherein the distal end of the shaft and a proximal end of the neck part are pivotally attached to allow the shaft to be tilted relative to the longitudinal axis of the neck part; and
   a locking mechanism having a proximal and distal end, the locking mechanism comprising:
      an engagement member having an engagement surface located at the distal end of the locking mechanism, wherein the engagement surface is positioned at the distal end of the hollow shaft and is ring-shaped and substantially perimetric to a longitudinal axis of the hollow shaft at the distal end of the shaft, wherein the engagement member is slideably mounted inside the hollow shaft and is configured to protrude from the distal end of the hollow shaft to urge the engagement surface against the proximal end of the neck part;
      a spring mounted proximally with respect to the engagement member, the spring being mounted inside the hollow shaft;
      a handle mounted at the proximal end of the locking mechanism, the handle being mounted outside the hollow shaft;
      a pair of arms extending from the proximal end to the distal end of the of locking mechanism such that the pair of arms are substantially parallel to the distal end of the hollow shaft, the pair of arms being mounted to the engagement member at the distal end of the locking mechanism and the handle at the proximal end of the locking mechanism, and the pair of arms extending through a respective hole of the pair of holes in the hollow shaft at the proximal end of the locking mechanism so that the handle is mounted outside the hollow shaft; and
   wherein the engagement member moveable distally to urge the engagement surface against the proximal end of the neck part to resist said tilting of the shaft relative to the longitudinal axis of the neck part, wherein the proximal end of the neck part includes a surface for engagement with the engagement surface of the engagement member, wherein said surface of the proximal end of the neck part is contained in a plane and said plane is oriented at a non-zero angle α with respect to the longitudinal axis of the neck part, where α<90°.

2. The acetabular reamer handle of claim 1, wherein the engagement member is resiliently biased distally to urge the engagement surface against the proximal end of the neck part.

3. The acetabular reamer handle of claim 2, wherein the spring comprises a helical spring further mounted coaxially with respect to the distal end of the hollow shaft.

4. The acetabular reamer handle of claim 1, wherein the handle is configured for manually retracting the engagement member in a proximal direction to release the engagement surface from the proximal end of the neck part.

5. The acetabular reamer handle of claim 1, comprising one or more locking members extending from the engagement surface to be received within one or more corresponding openings in the proximal end of the neck part for locking the engagement surface against the proximal end of the neck part to resist said tilting of the shaft relative to the longitudinal axis of the neck part.

6. The acetabular reamer handle of claim 1, wherein the acetabular reamer handle is an offset acetabular reamer handle in which the hollow shaft includes a proximal shaft section and a distal shaft section, in which the shaft has a bend located at an interface between the proximal shaft section and the distal shaft section.

7. The acetabular reamer handle of claim 6, wherein the proximal shaft section and the distal shaft section are rigidly formed whereby the angle between the longitudinal axis of the distal shaft section and a longitudinal axis of the proximal shaft section is fixed.

8. A surgical kit comprising the acetabular reamer handle of claim 1 and one or more differently sized acetabular reamers connectable to the head part of the acetabular reamer handle.

9. A method of reaming an acetabulum of a patient using a reamer connected to a reamer handle, the reamer handle comprising:
   a hollow shaft having a distal end and a wall with pair of holes extending therethrough;
   a hollow neck part having a longitudinal axis;
   a driveline extending through the shaft and the neck part, wherein a distally located head part of the driveline is mounted for rotation about the longitudinal axis of the neck part and is connected to the reamer, and wherein the distal end of the shaft and a proximal end of the neck part are pivotally attached to allow the shaft to be tilted relative to the longitudinal axis of the neck part; and
   a locking mechanism having a proximal and distal end, the locking mechanism comprising:
      an engagement member having an engagement surface located at the distal end of the locking mechanism, wherein the engagement surface is positioned at the distal end of the hollow shaft and is ring-shaped and substantially perimetric to a longitudinal axis of the hollow shaft at the distal end of the shaft, wherein the engagement member is slideably mounted inside the hollow shaft and is configured to protrude from the distal end of the hollow shaft to urge the engagement surface against the proximal end of the neck part;

a spring mounted proximally with respect to the engagement member, the spring being mounted inside the hollow shaft;

a handle mounted at the proximal end of the locking mechanism, the handle being mounted outside the hollow shaft;

a pair of arms extending from the proximal end to the distal end of the of locking mechanism such that the pair of arms are substantially parallel to the distal end of the hollow shaft, the pair of arms being mounted to the engagement member at the distal end of the locking mechanism and the handle at the proximal end of the locking mechanism, and the pair of arms extending through a respective hole of the pair of holes in the hollow shaft at the proximal end of the locking mechanism so that the handle is mounted outside the hollow shaft; and wherein the engagement member moveable distally to urge the engagement surface against the proximal end of the neck part to resist said tilting of the shaft relative to the longitudinal axis of the neck part, wherein the proximal end of the neck part includes a surface for engagement with the engagement surface of the engagement member, wherein said surface of the proximal end of the neck part is contained in a plane and said plane is oriented at a non-zero angle $\alpha$ with respect to the longitudinal axis of the neck part, where $\alpha<90°$, the method comprising:
  inserting the reamer into the acetabulum;
  operating the reamer to remove bone from a surface of the acetabulum; and
  with the reamer located in the acetabulum, tilting the shaft relative to the longitudinal axis of the neck part to view a part of the acetabulum and/or reamer otherwise obscured by the reamer handle.

10. The method of claim 9, further comprising operating the locking mechanism of the reamer handle to disengage the engagement member of the locking mechanism from the proximal end of the neck part to allow said tilting of the shaft relative to the longitudinal axis of the neck part.

11. The method of claim 9, wherein the engagement member is resiliently biased toward the proximal end of the head part.

12. The method of claim 9, wherein the reamer handle is an offset reamer handle in which the hollow shaft includes a proximal shaft section and a distal shaft section, in which the shaft has a bend located at an interface between the proximal shaft section and the distal shaft section.

\* \* \* \* \*